(12) United States Patent
Wu et al.

(10) Patent No.: US 10,413,655 B2
(45) Date of Patent: Sep. 17, 2019

(54) ARTIFICIAL LUNG SYSTEM AND ITS METHODS OF USE

(71) Applicants: UNIVERSITY OF MARYLAND, BALTIMORE, Baltimore, MD (US); BREETHE, INC., Baltimore, MD (US)

(72) Inventors: Zhongjun Wu, Marriottsville, MD (US); Bartley Griffith, Gibson Island, MD (US); David N. Wells, Silver Spring, MD (US)

(73) Assignees: UNIVERSITY OF MARYLAND, BALTIMORE, Baltimore, MD (US); BREETHE, INC, Halethorpe, MD (US)

( * ) Notice: Subject to any disclaimer, the term of this patent is extended or adjusted under 35 U.S.C. 154(b) by 288 days.

(21) Appl. No.: 15/598,947

(22) Filed: May 18, 2017

(65) Prior Publication Data

US 2017/0252505 A1 Sep. 7, 2017

Related U.S. Application Data

(63) Continuation of application No. PCT/US2015/061214, filed on Nov. 18, 2015.

(60) Provisional application No. 62/081,747, filed on Nov. 19, 2014.

(51) Int. Cl.
*A61M 1/36* (2006.01)
*A61M 1/16* (2006.01)

(52) U.S. Cl.
CPC ........ *A61M 1/3667* (2014.02); *A61M 1/1698* (2013.01); *A61M 1/3666* (2013.01); *A61M 2202/0208* (2013.01); *A61M 2205/8206* (2013.01); *A61M 2209/08* (2013.01); *A61M 2209/088* (2013.01)

(58) Field of Classification Search
CPC .............. A61M 1/1698; A61M 1/3666; A61M 1/3667; A61M 2202/0208; A61M 2205/8206; A61M 2209/08; A61M 2209/088
See application file for complete search history.

(56) References Cited

U.S. PATENT DOCUMENTS

| | | | |
|---|---|---|---|
| 7,682,327 B2 * | 3/2010 | Kirchhof | A61M 1/1698 422/44 |
| 2018/0169369 A1 * | 6/2018 | Ironstone | A61M 16/0078 |

* cited by examiner

*Primary Examiner* — Leslie R Deak
(74) *Attorney, Agent, or Firm* — Whiteford, Taylor & Preston, LLP; Gregory M. Stone

(57) ABSTRACT

An oxygen supply unit for use with a blood oxygenator comprises an oxygen concentrator and a carbon dioxide scrubber. In an on-line operational mode, oxygen-rich gas from the oxygen concentrator is predominantly supplied to the blood oxygenator with a reduced flow of recycled gas from the concentrator. In an off-line operational mode where the oxygen supply unit is being powered by battery only, a larger flow of recycled gas from the blood oxygenator is passed through the carbon dioxide scrubber and combined with a lesser amount of oxygen-rich gas from the oxygen concentrator. The oxygen supply unit may be used in combination with a blood pump and oxygenator to provide ambulatory blood oxygenation to patients with compromised lung function.

18 Claims, 7 Drawing Sheets

ARTIFICIAL LUNG SYSTEM AND ITS METHODS OF USE

CROSS REFERENCE TO RELATED APPLICATION

This application is a continuation of International PCT Application No. PCT/US2015/061214, filed in the United States Patent & Trademark Office as the Receiving Office on Nov. 18, 2015, which application claims the benefit of U.S. Provisional Application No. 62/081,747, filed Nov. 19, 2014, which applications are incorporated herein by reference.

GOVERNMENT LICENSE RIGHTS

This invention was made with government support under Grant number HL118372 awarded by the National Institutes of Health. The government has certain rights in the invention.

FIELD OF THE INVENTION

The present invention generally relates to systems and methods for oxygenating blood. More specifically, the invention relates to systems and methods for oxygenating blood in an ambulating patient.

BACKGROUND

Lung failure occurs acutely or chronically. Lung disease is the number three killer in the United States and is responsible for one in six deaths. Chronic obstructive pulmonary disease (COPD) is one of the most common lung diseases and is the fourth leading cause of death in the U.S. Adult Respiratory Distress Syndrome (ARDS) is afflicting 190,000 patients yearly and the average survival is between 30-50% (Rubenfeld et al. N Engl J Med 2005;353:1685-93). If lung failure occurs, either mechanical ventilation or extracorporeal membrane oxygenation (ECMO) must be implemented to oxygenate the blood to maintain the oxygen requirements of the body. Mechanical ventilation is effective for short-term support, yet the sustained tidal volumes and airway pressures often used may damage the lungs.

ECMO systems are an attractive alternative to mechanical ventilation since they closely simulate physiological gas exchange and extended ECMO support is possible via multiple device exchanges. But in practice, these systems are limited by the complexity of their operation, bleeding, and reduced patient mobility. The patients are often bedridden, resulting in muscular atrophy.

Recently, ambulatory ECMO support has been implemented in a number of centers using available pumps and oxygenators, allowing patients to walk around and go outside. They can also eat and exercise. In spite of the benefits that current ECMO systems provide, they are still very bulky. They are also limited for extended use due to the functional lifespan of oxygenators. In consideration of the limitations described above, there is a need in the art for a system and method for providing mechanical oxygenation for an ambulating patient using a portable artificial lung system that is suited for extended use.

Patents and published applications relevant to the subject matter of the present invention include US2013296633; US2011040241; U.S. Pat. No. 7,682,327; U.S. Pat. No. 6,935,344; U.S. Pat. No. 6,503,450; U.S. Pat. No. 5,308,320; U.S. Pat. No. 4,548,597; U.S. Pat. No. 4,610,656; and U.S. Pat. No. 3,927,981.

SUMMARY OF THE INVENTION

Techniques are provided for mechanical oxygenation of an ambulating patient using an artificial lung system that provides one or more advantages over the previously available oxygenation systems. While the systems of the present invention are particularly suitable as portable systems, they may also be used as or as part of stationary systems.

In a first set of embodiments, a blood oxygenation system includes a multi-lumen cannula that communicates with a pump oxygenator unit and a supply pack that provides a power source and an oxygen source. The pump oxygenator unit is configured to be disposable and removable from the rest of the system.

In one aspect of the invention, the pump oxygenator unit is configured to continuously oxygenate blood for more than thirty days without having to be replaced.

In another aspect of the invention, the blood is removed from the patient and returned to the patient through a dual lumen catheter which comprises a first lumen for removing non-oxygenated blood and a second lumen for returning oxygenated blood to the patient's circulatory system. The catheter may further comprise a self-sealing mechanism to allow for the cannula to be inserted directly into the right ventricle of the heart.

In yet another aspect of the invention, the supply pack is a portable unit that can include wheels to allow the patient to pull the unit.

In another variation, the supply pack has one or more straps to allow the patient to wear the pack as a backpack or satchel.

In another variation, the oxygen source may be an oxygen generator, an oxygen tank, or a combination of both.

In a second set of embodiments, a method of providing mechanical ventilation to an ambulating patient is provided which includes removing non-oxygenated blood from the circulatory system of a patient, passing the blood through a pump and oxygenator located on the body, and returning the newly oxygenated blood back to the circulatory system of the patient; wherein the pump communicates with a pump motor and controller that are separately housed in a portable pack; and wherein the oxygenator is supplied with oxygen from a portable source that is separately housed. The method optionally includes the use of a portable pack to house the pump motor, controller, and oxygen source. Alternatively, as illustrated hereinafter, the pump and/or the oxygenator may be carried on a belt worn around the patient's waist.

In another aspect, the present invention provides a compact, low-weight oxygen supply unit for a lung-assist oxygenator system that can deliver an oxygen flow rate typically in the range 0.5 to 3 liter per minute using a pressure-swing type oxygen concentrator in combination with a disposable carbon dioxide scrubber unit. The oxygen supply unit can run using battery power ("off-line" operation) or using AC or plug-in current ("on-line" operation). Use of the carbon dioxide scrubber increases battery life since the scrubber requires less power to recycle oxygen than does the oxygenation concentrator to produce oxygen. Not using the carbon dioxide scrubber while the system is powered from an external source, however, is preferable since the power source is unlimited and the life of the carbon dioxide scrubber can be extended (the scrubbing medium is not being consumed), allowing use of a smaller scrubber and/or less frequent scrubber exchange. In this way, the size and weight of the oxygen supply unit can be minimized and the battery operation time maximized.

During off-line or battery operation, oxygen-rich gas from the oxygen supply unit enters the blood oxygenator where it exchanges oxygen for carbon dioxide and produces an exhaust gas having an increased carbon dioxide content. The amount of carbon dioxide, however, is not great. Rather than dumping this exhaust gas which still contains a high level of oxygen into the environment, the gas can be returned to the oxygen supply unit where it is scrubbed to remove the carbon dioxide, typically after removing water vapor. The scrubbed gas is recycled back to the blood oxygenator unit with the addition of a small flow of concentrated oxygen from the oxygen concentrator unit sufficient to replace the amount of oxygen which was transferred during the previous passage through the blood oxygenator. In this way, a high oxygen rich gas flow rate, on the order of 5 to 10 liters per minute, can be provided to the oxygenator using only 0.5 to 1 liters per minute of oxygen from the oxygen concentrator to reduce power consumption and extend battery life.

When the patient is able to plug in the oxygen supply unit ("on-line" operation), power consumption is no longer a concern and output of the oxygen concentrator is increased, allowing flow though the carbon dioxide scrubber to be bypassed. Consumption of scrubbing medium is thus prevented during on-line operation, so the size or the scrubber can be reduced and/or the usable life of the scrubber can be extended, minimizing the replacement frequency. The size of the oxygen supply unit can be further minimized by using a relatively low output 0.5-3 liter per minute oxygen concentrator in combination with the disposable carbon dioxide scrubber canister, making the dual operation mode oxygen supply unit of the present invention cheaper, smaller, and lighter in total size and weight than an equivalent battery-only system where the carbon dioxide scrubber must be sized to accommodate constant operation.

In accordance with a particular method of the present invention, an oxygen-rich gas stream useful for blood oxygenation may be produced by selectively operating an oxygen concentrator from either battery power or an external power source, typically line power from the grid or from a local generator. Oxygen from the oxygen concentrator will be delivered without scrubbing to a blood oxygenator when the oxygen concentrator is operating from the external power source. In contrast, oxygen from the oxygen concentrator will be combined with a carbon dioxide-scrubbed oxygen gas stream, and the combined gas stream delivered to the blood oxygenator, when the oxygen concentrator is operating from the battery. In this way, battery life can be increased while simultaneously extending the life of and/or reducing the size of the carbon dioxide scrubber which is utilized.

In some embodiments, the carbon dioxide-scrubbed gas stream is produced by scrubbing carbon dioxide from a carbon dioxide elevated gas stream received from the blood oxygenator. Usually, the oxygen concentrator delivers a flow in the range from about 0.5 liters per minute (LPM) to 1 LPM to combine with the carbon dioxide-scrubbed gas stream. Usually, the carbon dioxide-scrubbed gas flow is in the range from 4.5 LPM to 9 LPM.

In embodiments where oxygen from the oxygen concentrator is delivered to the blood oxygenator without scrubbing, the oxygen is delivered at a rate in the range from 2 LPM to 6 LPM. In such instances, the oxygen from the oxygen concentrator may be further combined with a carbon dioxide-elevated gas stream from the blood oxygenator. In these instances, as a higher oxygen flow rate is provided by the oxygen concentrator, there is no need to scrub the carbon-dioxide elevated gas stream as is the case during off-line operation. The carbon dioxide elevated gas stream will usually be combined with the oxygen from the oxygen concentrator at a rate from 3 LPM to 6 LPM.

In accordance with a particular apparatus of the present invention, an oxygen supply unit intended for use with a blood oxygenator comprises an oxygen concentrator, a carbon dioxide scrubber, a power control, and a valved tubing network. The oxygen concentrator is configured to produce a concentrated oxygen stream from air, typically comprising a pressure-swing oxygen concentrator driven by an internal electrical compressor. The carbon dioxide scrubber is configured to receive a "recycled" stream of elevated carbon dioxide gas flow from the blood oxygenator and to remove or "scrub" carbon dioxide from that stream, typically removing substantially all carbon dioxide. As the recycled elevated carbon dioxide gas flow from the blood oxygenator will still comprise well over 90% of the oxygen originally present, once the carbon dioxide is removed, it is suitable for return to the blood oxygenator after it is combined with an amount of oxygen from the oxygen concentrator which is sufficient to replace that which has been removed during the previous pass of the gas stream through the blood oxygenator. The power control is configured to selectively deliver power from either a battery source or an external power supply, typically an AC wall plug available in most places. The valve tubing network is configured to deliver oxygen-rich gas from the oxygen concentrator to the blood oxygenator without scrubbing when the power control delivers power from the external power supply to the oxygen supply unit. The valve tubing network is further configured to combine oxygen-rich gas from the oxygen concentrator with the carbon dioxide-scrubbed gas being recycled from the carbon dioxide scrubber when the power control delivers power from the battery. Such dual-mode operation has the advantages of power efficiency and reduced scrubbing medium consumption as described above in connection with the methods of the present invention.

The oxygen supply units of the present invention will typically be enclosed within a shell or an enclosure, and the shell or enclosure typically comprises wheels configured to allow the enclosure to be pulled or pushed by a user. Alternatively, the enclosure could be configured to be worn as a backpack (optionally by an individual other than the patient), mounted on a wheel chair, mounted in a car, airplane, or other vehicle, or the like. Still further alternatively, the enclosure could be configured for stationary placement.

The carbon dioxide scrubber may be a conventional canister-type scrubber having a commercially available scrubbing medium, such as a soda lime, suitable media being commercially available under the trade names Litholyme®, Sodasorb®, Medisorb®, Sodasorb® LF, and Amsorb®.

The valved tubing networks of the oxygen supply units of the present invention will typically further comprise a dehumidifier for removing moisture from the elevated carbon dioxide gas flow prior to that gas flow passing through the carbon dioxide scrubber. Useful dehumidifiers include commercially available Nafion® gas driers. The valved tubing networks will usually further comprise a pump for flowing the elevated carbon dioxide gas stream through the carbon dioxide scrubber and combining the gas stream with the oxygen stream from the concentrator which is at a relatively higher pressure. Other features of the valved tubing network include a bypass line which allows the oxygen-rich gas to flow by the carbon dioxide scrubber during online operation. Still other features include disconnects which allow the carbon dioxide scrubbing canister to be removed and replaced from the oxygen supply unit with minimal difficulty.

The oxygen supply units of the present invention, as described above, may be combined with a pump-blood oxygenator unit configured to be worn by a patient. The blood pump oxygenator units typically include a blood-oxygenator having a semi-permeable membrane matrix allowing oxygen-carbon dioxide exchange as blood and the oxygen-rich air stream flow through the oxygenator. These systems will typically further comprise an umbilical cord or cable for connecting the oxygen supply unit to the blood-pump oxygenator. The umbilical cord will include tubes for delivering the oxygen-rich gas from the oxygen supply unit to the pump-blood oxygenator as well as for returning elevated carbon dioxide gas from the blood pump oxygenator to the oxygen supply unit. The umbilical cables will still further include electrical lines for delivering power and/or control signals from the oxygen supply unit to the blood-pump oxygenator.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

A method and system are described for the long term mechanical oxygenation of an ambulating patient. In the following description, for the purpose of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

The system of the present invention provides a long-term solution to enable a person in need of blood oxygenation, the ability to no longer be bed ridden. The system comprises a pump oxygenator unit that interfaces with the patient's circulatory system via a multi-lumen cannula. The pump oxygenator unit is capable of oxygenating blood for an extended period of time. A portable supply pack provides the necessary power and oxygen source to the system.

Figure 1:
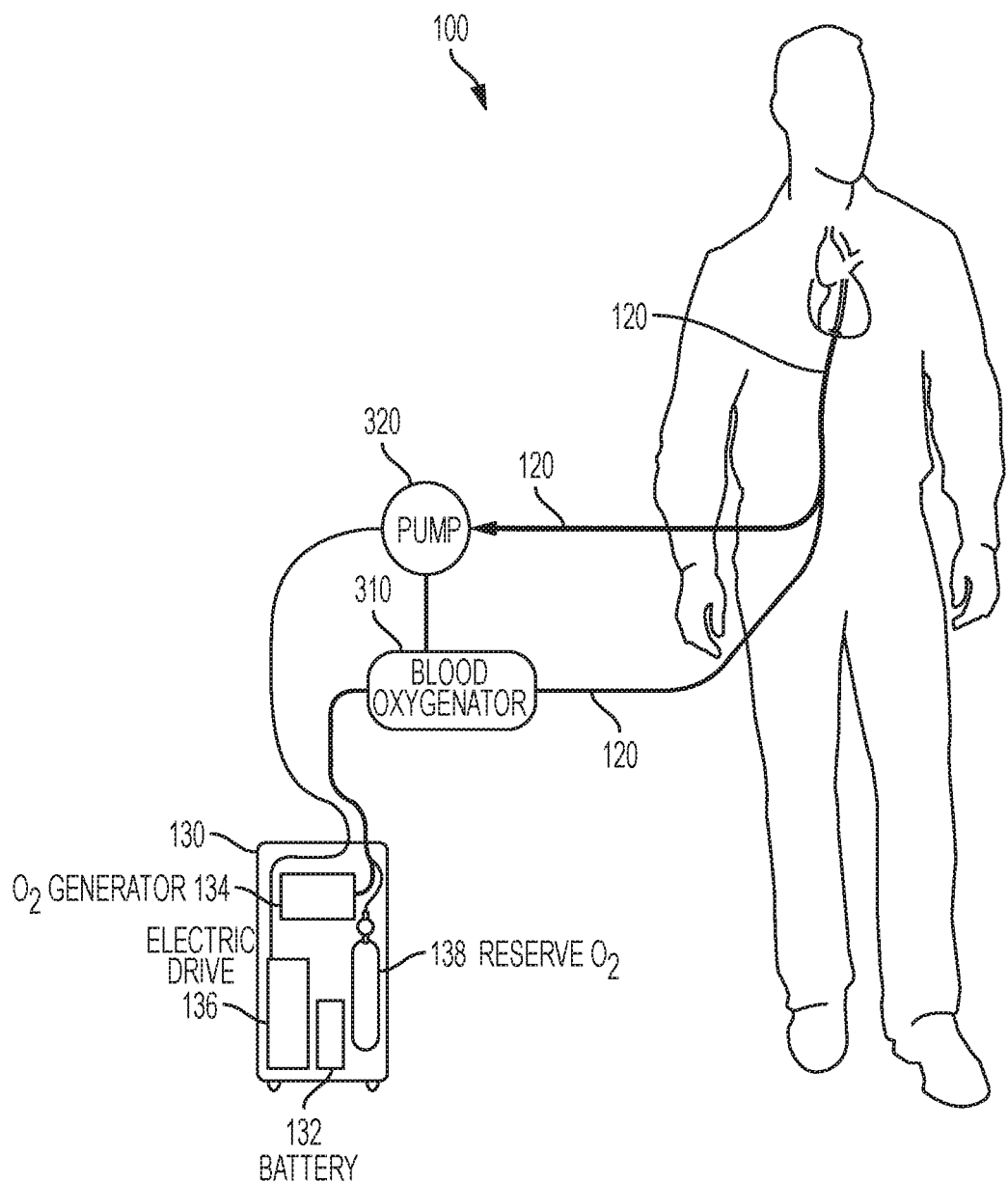
FIG. 1 illustrates one example configuration of an ambulatory blood pump oxygenation system including an oxygen supply unit and a pump oxygenator combination.
Figure 2:
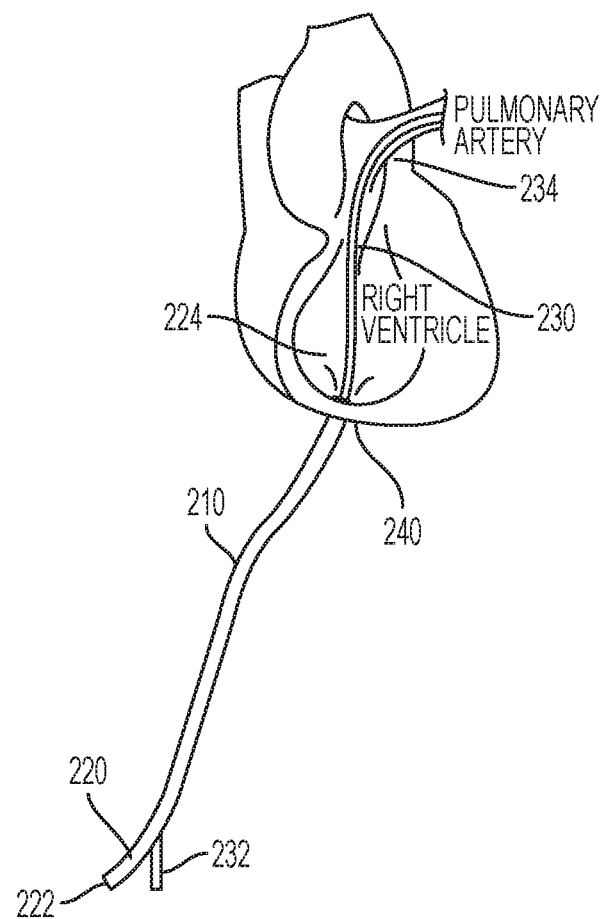
FIG. 2 depicts one example configuration of the cannula that introduces oxygenated blood and removes non-oxygenated blood from the circulatory system.

Referring now to the figures, FIG. 1 depicts one embodiment of the portable blood oxygenator system, 100. System 100 comprises a multi-lumen cannula 120, blood oxygenator 310, blood pump 320, and a portable supply pack 130. One example embodiment of the multi-lumen cannula 120 is further depicted in FIG. 2. In this example, cannula 120 comprises an elongated body 210 having a drainage cannula and a return cannula. Drainage cannula 220 and return cannula 230 have inner lumens, both of which run the length of the elongated body. Drainage cannula 220 has a proximal end 222 and a distal end 224. Return cannula 230 also has a proximal end 232 and a distal end 234. The proximal ends of the drainage and return cannulas are configured to communicate with pump oxygenator combination 310/320. The connections between the ends of the cannulas and the pump oxygenator unit are detachable. Drainage cannula 220 is configured to receive non- oxygenated blood from the right ventricle of the heart and send it back to the pump oxygenator unit. The return cannula is configured to return oxygenated blood into the pulmonary artery from the pump oxygenator unit. Cannula 120 further comprises a self-sealing mechanism 240 near the distal end to prevent blood leakage from the heart where the cannula is inserted. In certain embodiments, self-sealing mechanism 240 is detachable from the elongated body.

Figure 3:
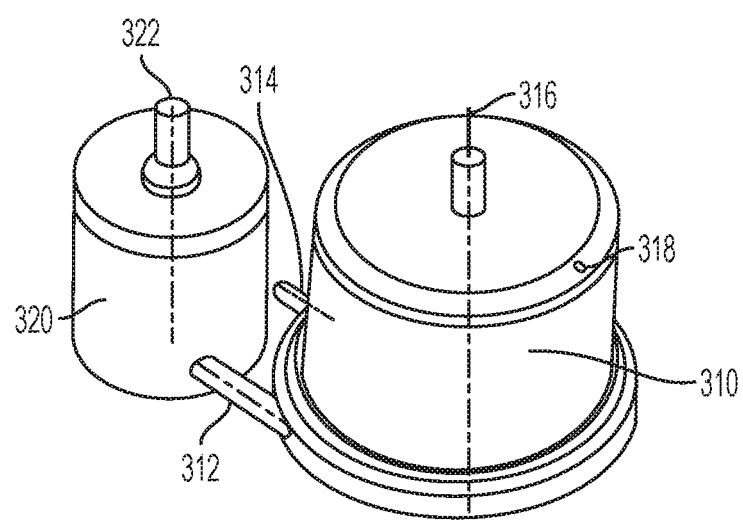
FIG. 3 illustrates one example configuration of the pump oxygenator unit.

FIG. 3 depicts one example configuration of a pump oxygenator unit. The unit comprises a blood oxygenator 310 and blood pump 320. The blood oxygenator may be any blood oxygenator known in the art. However, in certain embodiments, a blood oxygenator that provides uniform blood flow and oxygen diffusion is preferred. In the illustrated embodiment, blood pump 320 includes an inlet 322 that is configured to receive non-oxygenated blood from drainage cannula 220. The non-oxygenated blood travels from the blood pump and into the oxygenator through oxygenator inlet 312. Oxygen which is received from the oxygen source at gas inlet 314 is diffused into the blood as it travels through the oxygenator. Once oxygenated, the blood travels through outlet 316 which communicates with return cannula 230. Exhaust gas is released through outlet 318. The blood pump communicates with the electric motor drive located in the supply pack as described below. This connection is detachable at the pump in certain embodiments.

Supply pack 130 houses a power source 132, an electric motor drive 136 and one or more oxygen sources 138. The supply pack is configured to be a portable system that can readily be moved and transported by the user. In certain embodiments, the supply pack housing includes wheels and a handle to allow the user to pull the unit. However, the supply pack may also be housed in a wearable case such as a backpack, satchel, or waste pouch. Power source 132 is configured for long-term, portable use. Any type of battery may be used to power the system including both rechargeable and non-rechargeable options.

Oxygen may be supplied to the patient by oxygen generator 134 or an oxygen source 138. In certain embodiments, the supply pack includes an oxygen generator as well as an oxygen source that may be used as a reserve. Oxygen source 138 is generally a compressed gas tank that includes a regulator at the outlet to control the volume and rate of oxygen that is released into the system. A series of oxygen tanks may be used in certain embodiments. The size and number of oxygen sources, or tanks that are housed in the supply pack will depend on the user's needs. Electric motor drive 136 is powered by power source 132 and operates pump oxygenator unit 110. A controller communicates with pump 320 via a cable that runs from the supply pack to the pump. The controller is responsible for varying the motor speed to maintain the oxygen needs of the user.

Blood oxygenators must be replaced periodically due to thrombosis that occurs on the membranes that allow for gas transfer. In certain embodiments, the pump oxygenator unit is separate from the electric motor drive to allow for the replacement of the pump oxygenator unit without having to replace the more costly electric motor drive. The pump oxygenator unit is capable of continued use for thirty days or more. When replacing the pump oxygenator unit, the cannula is removed from inlet 322 and outlet 316. The electric motor drive is also detached from the pump and the oxygen source is detached at 314. In other embodiments, the oxygenator is the only element of the system that must be replaced on a regular basis.

Another aspect of the present invention provides a method of providing permanent mechanical oxygenation to an ambulating patient in need. The method includes (a) directing non-oxygenated blood from the circulatory system of a patient through an inlet in a pump and an oxygenator; and (b) returning the oxygenated blood to the circulatory system of said patient; wherein the pump and oxygenator are part of a portable system which comprises a portable power source and oxygen source housed in a pack. In one variation of the method, the blood oxygenator is capable of continuously oxygenating blood for more than thirty days.

Figure 4A:
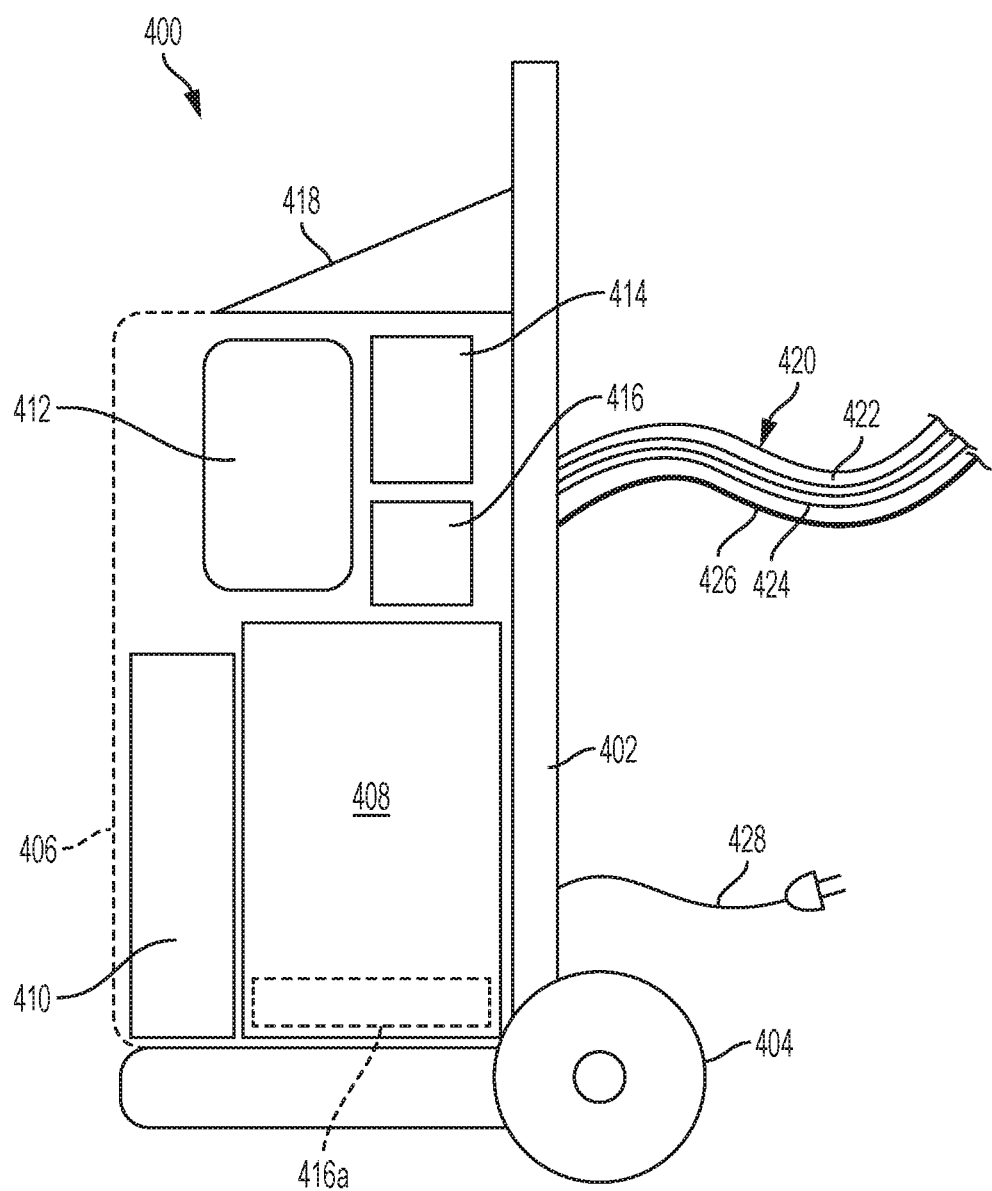
FIG. 4A illustrates an alternate embodiment of an ambulatory oxygen supply unit of the present invention including an oxygen concentrator in place of an oxygen tank.
Figure 4B:
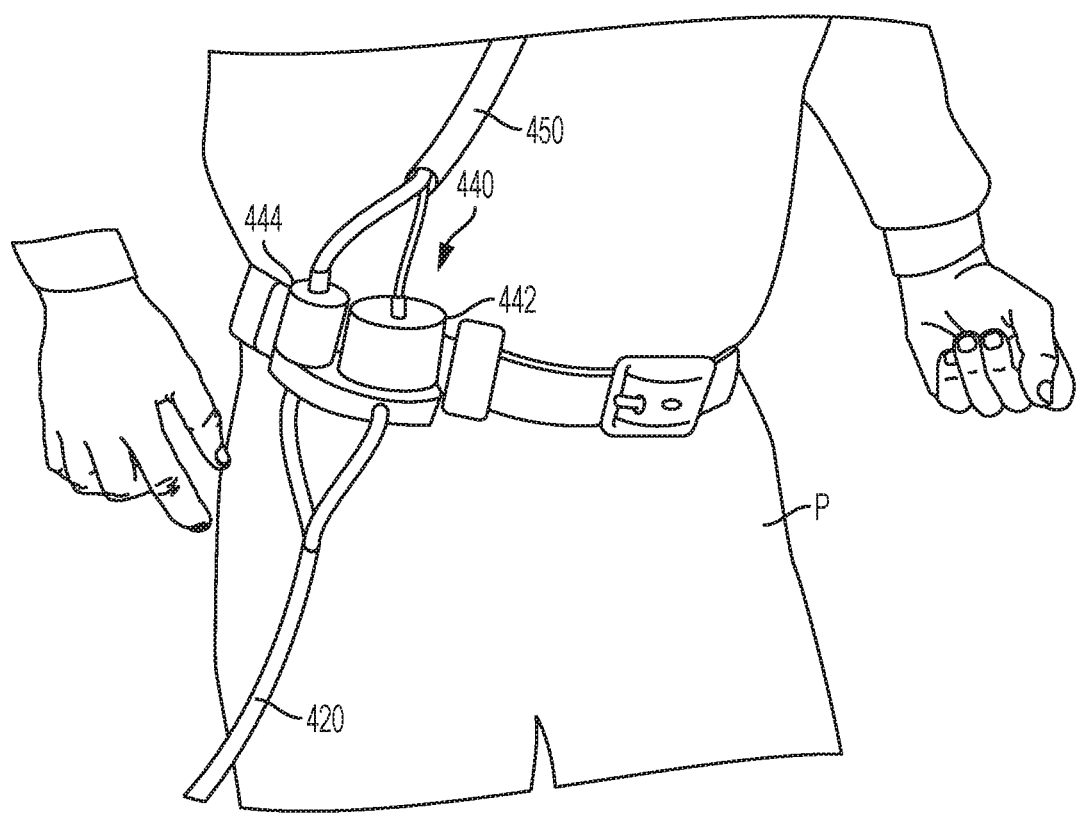
FIG. 4B illustrates a pump oxygenator unit secured to a patient's waist on a belt showing an umbilical suitable for connecting to an ambulatory oxygen supply unit.

Referring now to FIG. 4A, an alternative embodiment of an oxygen supply unit constructed in accordance with the principles of the present invention comprises a frame 402 which is typically mounted on wheels 404 to allow mobility and easy repositioning. A shell or enclosure 406 is typically provided in order to enclose a plurality of system components, including an oxygen concentrator 408, a battery 410, a carbon dioxide scrubber 412, a recirculating pump 414, a dehumidifier 416, and a control unit 418. The oxygen concentrator may be a commercial unit selected to provide a concentrated oxygen flow in the desired flow range, typically from 1 LPM to 3.5 LPM. Typically, the oxygen concentrator will employ the pressure-swing principle which divides the air into a high oxygen concentration stream and a high nitrogen concentration stream. The high oxygen concentration stream will be used and the nitrogen stream released back to the atmosphere. The battery may be any conventional rechargeable battery, typically being a lithium ion battery or the like. The carbon dioxide scrubber will typically comprise a canister filled with a soda lime or other scrubbing medium, as has been previously described herein. The recirculation pump will be used in order to deliver elevated carbon dioxide gas from the blood oxygenator to the scrubber, as will be described in more detail below. The dehumidifier is typically a coil which condenses out water from the recycled elevated carbon dioxide stream from the blood oxygenator, e.g., a Nafion® gas dryer. In some embodiments, the dryer 416 is located above the oxygen concentrator 408, as shown in full line. In other embodiments, the dryer 416a is located below the oxygen concentrator, as shown in broken line, thus exposing the dryer tubes directly to hot gas produced by the concentrator. The latter design is an advantage as it avoids ducting which is necessary if the dryer is above the concentrator, allowing a more compact design. The control unit will typically provide an operator interface and also include control circuitry and logic which manages the valving system and power distribution system as described in more detail below with respect to FIGS. 5A and 5B. The umbilical cord 420 provides for convenient attachment to the pump-blood oxygenator unit (or pump oxygenator unit) 440 (FIG. 4B) which is worn by the patient. The umbilical cord includes an oxygen-rich gas line 422, an elevated carbon dioxide gas line 424, and one or a plurality of power/control line(s) 426. In addition, a plug-in power line 428 will be provided for use when it is possible to plug the unit into an AC or other external power source. Referring now to FIG. 4B, a pump oxygenator unit 440 may be worn by the patient P, for example on a belt at the patient's waist. The pump oxygenator unit 440 will include a blood oxygenator 442 and a blood pump 444. The pump 444 receives venous blood from the patient and delivers the venous blood into the blood oxygenator 442. Oxygenated blood from the oxygenator 442 returns back to the patient on the arterial side of the vasculature. For example, a cannula 450 may be used for delivering blood to and from the patient, as described in copending application PCT/US2015/060127, for "Self-Sealing Cannula," filed on Nov. 13, 2015, the full disclosure of which is incorporated herein by reference.

Figure 5A:
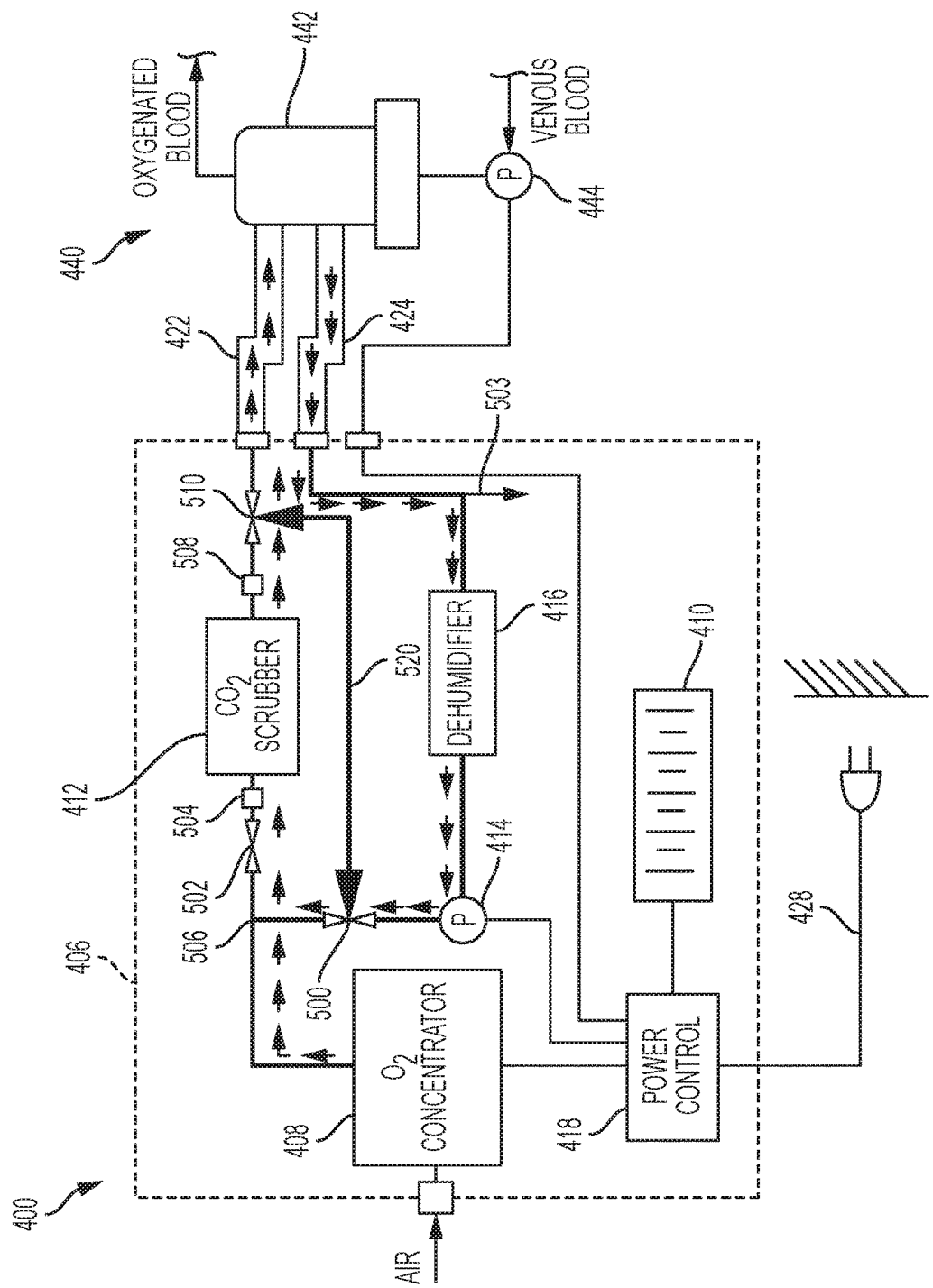
FIGS. 5A and 5B illustrate operation of the oxygen supply unit of FIG. 4 including selective carbon dioxide scrubbing and battery/plug-in operation.

Referring now to FIG. 5A, the layout of the components of the oxygen supply unit 400 will be described in more detail. The oxygen concentrator 408 is mounted within the enclosure 406 and connected to the ambient to receive an inflow of air. Power is delivered to the oxygen concentrator 408 from a power control unit 418, and may be either power from the battery 410 or from the line cord 428. As shown in FIG. 5A, the power is coming from the battery 410 as the line cord 428 is not connected. The power control may be configured to automatically detect the power source based on whether or not the line cord 428 is connected to an AC current source. When the oxygen supply unit 400 is not connected to the AC power source, elevated carbon dioxide gas entering through line 424 passes through the dehumidifier 416 and is pumped by recirculating pump 414 through a control valve 500 which directs the elevated carbon dioxide gas to the carbon dioxide scrubber 412 through a second valve 502 and a quick disconnection fitting 504. A vented T-fitting 503 is optionally provided to exhaust excess elevated carbon dioxide gas from the system to the ambient.

The vented elevated carbon dioxide gas volume will be equal to the net inflow volume from the oxygen concentrator 408. Other excess gas exhaust mechanisms might also be used. Often, there will be liquids in carbon dioxide gas line 424 exiting the oxygenator unit 442, including condensed water vapor and a small amount of blood plasma. A separator (not shown) will typically be provided as part of the oxygen supply unit 400 or alternatively in the supply line 424 to remove these liquids.

The elevated carbon dioxide gas from pump 414 combines with oxygen from the oxygen concentrator 408 through a T-junction 506. As described previously, from 4.5 LPM to 6 LPM of the elevated carbon dioxide gas will typically pass through the carbon dioxide scrubber with the addition of approximately 1 LPM of oxygen-rich gas from the oxygen concentrator 408. The relative amounts delivered can be controlled via the pump 414. Scrubbed oxygen-rich gas from the carbon dioxide scrubber 412 passes out through a quick disconnect 508 and further control valve 510 which allows the gas to pass into the oxygen-rich gas line 422 back to the blood oxygenator 442. Gas flow may continue in this pattern for so long as the blood supply unit 400 remains disconnected from AC power. In this efficient operational mode, the battery life will typically last at least several hours, and may last as many as 4 hours, 5 hours, 6 hours, or longer.

Figure 5B:
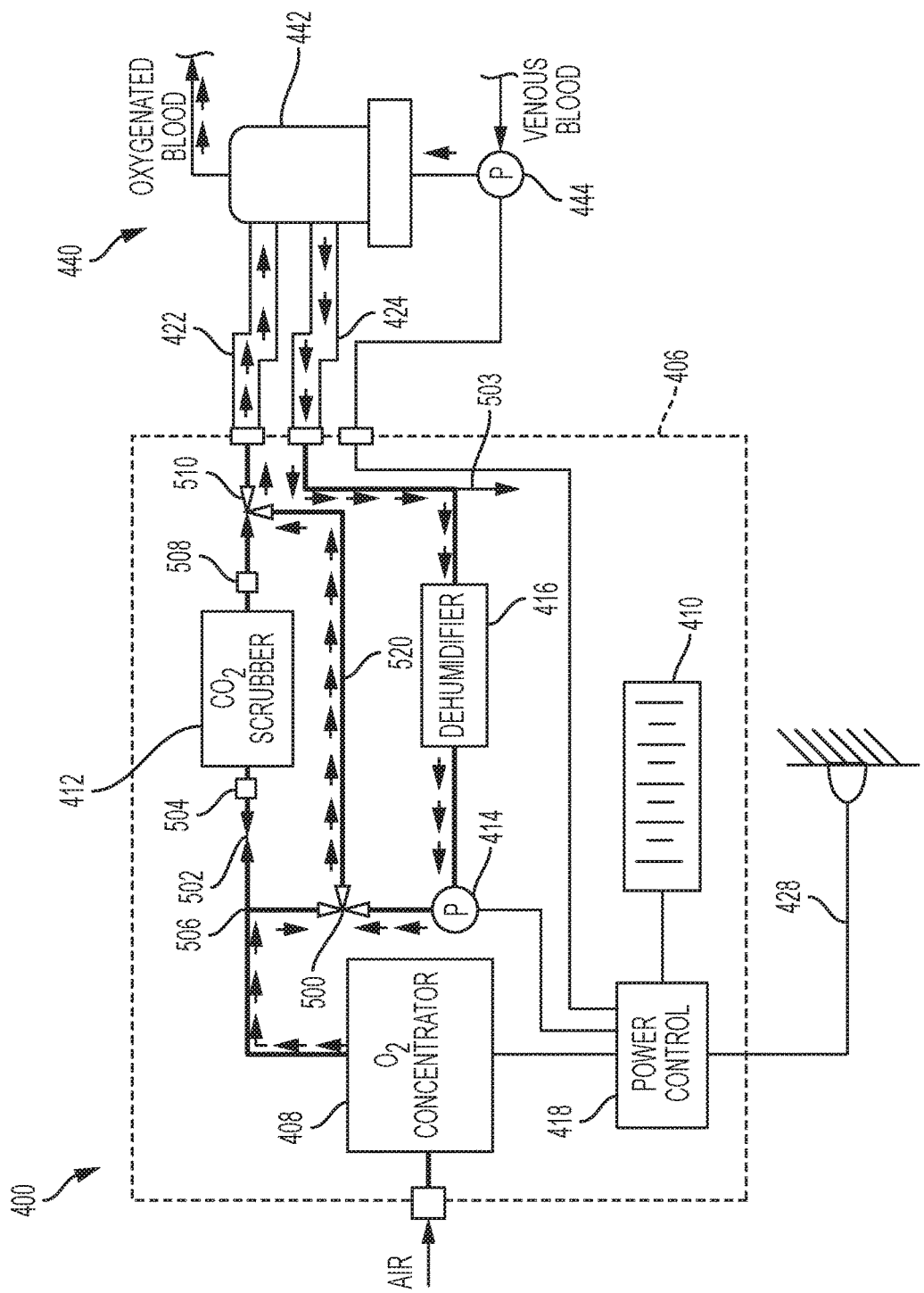

Once the patient reaches a location where AC or other external power is available, the user may plug the power line into an AC power source, as shown in FIG. 5B. Once line current is available, operation of the oxygen supply unit 400 may be changed in order to preserve the carbon dioxide scrubbing media to extend the life of the scrubber and/or reduce the size of the scrubber. In particular, oxygen from the oxygen concentrator will now bypass the carbon dioxide scrubber through a bypass line 520 which was previously isolated by valves 500 and 510. Valves 500 and 510 are now reconfigured to allow passage of the oxygen-rich gas through the bypass line 520. Similarly, valves 502 and 510 are arranged to block flow through the $CO_2$ scrubber. While in this configuration, the carbon dioxide scrubber 412 may be removed and replaced using the quick disconnect elements 504 and 508. During online operation, the volume of oxygen-rich gas from the oxygen concentrator will be increased, typically to the range from 2.5 LPM to 3.5 LPM. Elevated carbon dioxide gas entering through line 424, however, will continue to be recycled and mixed with the oxygen- rich gas, although at a lower flow rate, typically in the range from 3 LPM to 6 LPM. Mixing occurs in valve 500 and the relative flow volumes can again be controlled using pump 414. The combined rich oxygen gas stream and elevated carbon dioxide gas stream flow through the bypass line 520 and out through valve 510 where they can enter oxygen-rich gas line 422 and return to the blood oxygenator 442.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for providing oxygen rich gas for blood oxygenation, said method comprising:
   selectively operating an oxygen concentrator from battery power or from an external power source;
   delivering oxygen from the oxygen concentrator without scrubbing to a blood oxygenator when the oxygen concentrator is operating from the external power source; and
   combining oxygen from the oxygen concentrator with a carbon dioxide-scrubbed oxygen gas stream and delivering the combined gas stream to the blood oxygenator when the oxygen concentrator is operating from the battery.

2. A method as in claim 1, further comprising producing the carbon dioxide-scrubbed gas stream by scrubbing carbon dioxide from a carbon dioxide elevated gas stream received from the blood oxygenator.

3. A method as in claim 2, wherein the oxygen concentrator delivers a flow in the range from 0.5 LPM to 1 LPM to combine with the carbon dioxide-scrubbed gas stream.

4. A method as in claim 3, wherein the carbon dioxide-scrubbed gas flow is from 4.5 to 9 LPM.

5. A method as in claim 1, wherein oxygen from the oxygen concentrator without scrubbing is delivered at a rate from 2 LPM to 6 LPM.

6. A method as in claim 5, further comprising combining the oxygen from the oxygen concentrator with a carbon dioxide elevated gas stream from the blood oxygenator.

7. A method as in claim 6, wherein the carbon dioxide elevated gas stream flows at a rate from 3 LPM to 6 LPM.

8. An oxygen supply unit for a blood oxygenator which receives an oxygen rich gas flow and generates an elevated carbon dioxide gas flow, said oxygen supply unit comprising:
   an oxygen concentrator which produces an oxygen rich gas stream from air;
   a carbon dioxide scrubber which removes carbon dioxide from an elevated carbon dioxide gas flow;
   a power control which selectively delivers power from a battery or an external power supply; and
   a valved tubing network configured (1) to deliver oxygen rich gas from the oxygen concentrator to the blood oxygenator without scrubbing when the power control delivers power from the external power supply and (2) to combine oxygen rich gas from the oxygen concentrator with carbon dioxide-scrubbed gas from the carbon dioxide scrubber when the power control delivers power from the battery.

9. An oxygen supply unit as in claim 8, further comprising an enclosure wherein the oxygen concentrator, the carbon dioxide scrubber, the power control, and the valved tubing network are disposed within the enclosure.

10. An oxygen supply unit as in claim 9, wherein the enclosure comprises wheels configured to allow the enclosure to be pulled or pushed by a user.

11. An oxygen supply unit as in claim 8, wherein the oxygen concentrator comprises a pressure-swing oxygen concentrator having an electronically driven internal compressor.

12. An oxygen supply unit as in claim 8, wherein the carbon dioxide scrubber includes a canister having a scrubbing medium.

13. An oxygen supply unit as in claim 12, wherein the scrubbing medium comprises soda lime, Litholyme®, Sodasorb®, Medisorb®, Sodasorb® LF, and Amsorb®.

14. An oxygen supply unit as in claim 8, wherein the valved tubing network comprises a dehumidifier for removing moisture from the elevated carbon dioxide gas flow prior to passing said flow through the carbon dioxide scrubber.

15. An oxygen supply unit as in claim 14, wherein the valved tubing network further comprises a pump for flowing the elevated carbon dioxide gas stream.

16. An oxygen supply unit as in claim 15, wherein the valved tubing network further comprises a bypass line which allows the oxygen rich gas to flow by the carbon dioxide scrubber.

17. A system comprising:
   an oxygen supply unit as in claim 8; and
   a pump-blood oxygenator unit configured to be worn by a patient.

18. A system as in claim 17, further comprising an umbilical cable including an oxygen rich flow tube, an elevated carbon dioxide flow tube, and an electrical line which connects a pump of the pump-blood oxygenator unit to the power control of the oxygen supply unit.

* * * * *